(12) United States Patent
Aki et al.

(10) Patent No.: US 7,413,880 B2
(45) Date of Patent: Aug. 19, 2008

(54) TEST KIT FOR IMMUNOCHROMATOGRAPHY

(75) Inventors: Masako Aki, Kobe (JP); Shinya Nagai, Akashi (JP); Takeshi Imoarai, Kobe (JP)

(73) Assignee: Sysmex Corporation, Kobe-shi, Hyogo (JP)

( * ) Notice: Subject to any disclaimer, the term of this patent is extended or adjusted under 35 U.S.C. 154(b) by 190 days.

(21) Appl. No.: 11/329,063

(22) Filed: Jan. 11, 2006

(65) Prior Publication Data

US 2006/0154301 A1 Jul. 13, 2006

(30) Foreign Application Priority Data

Jan. 12, 2005 (JP) .............................. 2005-005394

(51) Int. Cl.
*G01N 33/53* (2006.01)

(52) U.S. Cl. .................. 435/100; 436/514; 436/518; 436/807; 436/808; 436/810; 422/56; 422/61; 422/100; 422/102; 422/104

(58) Field of Classification Search .................. 422/61, 422/56, 100, 102, 104; 436/514, 518, 807, 436/808
See application file for complete search history.

(56) References Cited

U.S. PATENT DOCUMENTS

| | | | | |
|---|---|---|---|---|
| 4,205,058 A | * | 5/1980 | Wagner et al. | 436/500 |
| 4,235,601 A | * | 11/1980 | Deutsch et al. | 436/514 |
| 4,510,119 A | * | 4/1985 | Hevey | 422/71 |
| 5,077,194 A | * | 12/1991 | Heeny et al. | 435/5 |
| 5,132,232 A | * | 7/1992 | Parker | 436/177 |
| 5,177,021 A | * | 1/1993 | Kondo | 436/518 |
| 5,290,678 A | * | 3/1994 | Jackowski | 435/7.4 |
| 5,512,432 A | * | 4/1996 | Lapierre et al. | 435/5 |
| 6,180,417 B1 | | 1/2001 | Hajizadeh et al. | |
| 6,194,221 B1 | | 2/2001 | Rehg et al. | |
| 6,403,383 B1 | * | 6/2002 | Casterlin et al. | 436/518 |
| 6,461,873 B1 | * | 10/2002 | Catania et al. | 436/518 |
| 6,599,481 B2 | * | 7/2003 | Savitz et al. | 422/102 |
| 2005/0130120 A1 | * | 6/2005 | Lambotte et al. | 435/4 |

FOREIGN PATENT DOCUMENTS

JP 10-68730 A 3/1998

* cited by examiner

*Primary Examiner*—Bao-Thuy L. Nguyen
(74) *Attorney, Agent, or Firm*—Sughrue Mion, PLLC

(57) ABSTRACT

A test kit for immunochromatography comprising a test strip and a test tube is described. The test strip comprises a detection zone for detecting an analyte in a sample. The test tube accommodates the test strip. The test tube comprises an indicator at a position corresponding to the detection zone of the test strip which is inserted into the test tube.

19 Claims, 12 Drawing Sheets

(a)   (b)

(a)   (b)

Fig. 6
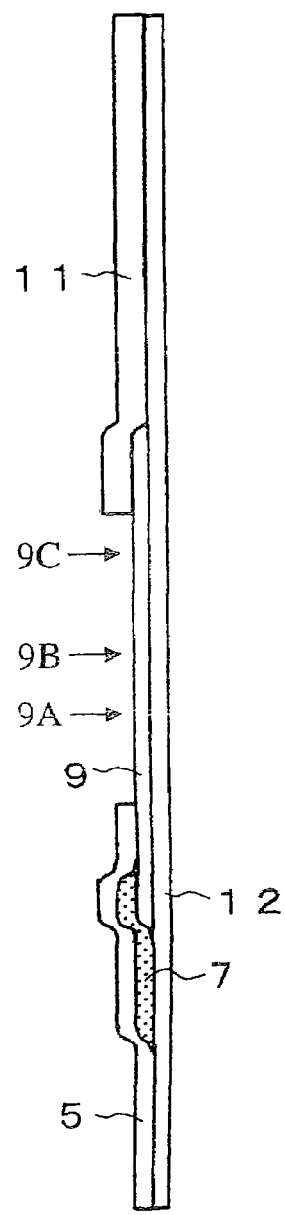
(a)
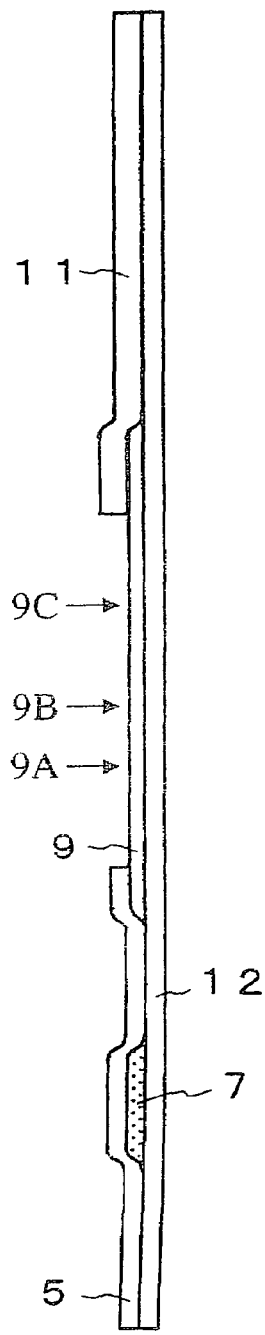
(b)
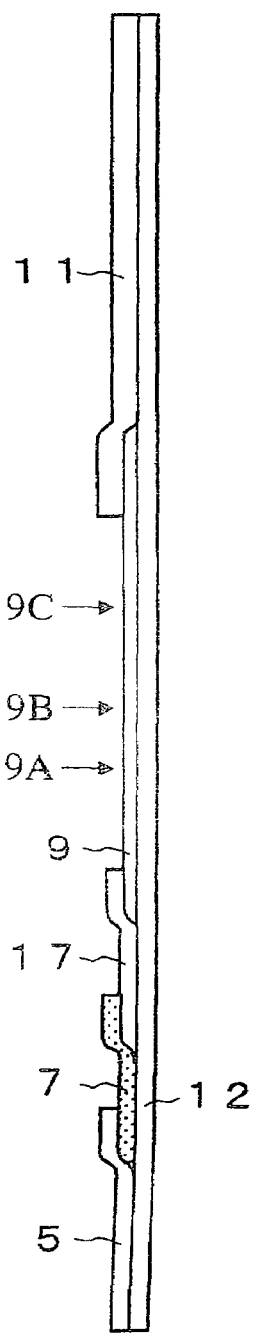
(c)

TEST KIT FOR IMMUNOCHROMATOGRAPHY

TECHNICAL FIELD

The present invention relates to a test kit for immunochromatography.

BACKGROUND

As a method for easily performing the tests for a variety of diseases using body fluid such as blood, serum, pharynx swab or the like, there is an immunochromatography.

As a test strip used for immunochromatography, a test strip which is equipped with a chromatography membrane is known. This test strip is equipped with a detection zone that traps the analyte in a sample, and the indicator showing at which position the analyte is trapped has been printed. As a test strip in which the indicator has been printed on the chromatography membrane, for example, a test strip described in JP Laid-Open Patent No. 2001-013143 is known.

By this method, since the working process of printing the indicator on the chromatography membrane becomes necessary, the manufacturing of the test strip becomes complex, and the cost becomes high.

Moreover, according to this method, an ink or the like used for printing may have a bad influence on the detection of the analyte. Furthermore, it may damage the chromatography membrane at the time of printing, and this damage may have a bad influence on the detection of the analyte.

An object of the present invention is to provide a test kit for immunochromatography which can be prepared easily and at a low cost and in which the analyte can be precisely detected.

SUMMARY

The present invention provides a test kit for immunochromatography and a test tube for immunochromatography.

The scope of the present invention is defined solely by the appended claims, and is not affected to any degree by the statements within this summary.

A first aspect of the present invention relates to a test kit for immunochromatography comprising:

a test strip comprising a detection zone for detecting an analyte in a sample; and a test tube for accommodating the test strip, wherein the test tube comprises an indicator at a position corresponding to the detection zone of the test strip which is inserted into the test tube.

A second aspect of the present invention relates to a test tube which can accommodate a test strip for immunochromatography, comprising an indicator that indicates a type of an analyte detected by a detection zone of the test strip at a position corresponding to the detection zone of the test strip.

BRIEF DESCRIPTION OF THE DRAWINGS

FIG. 2 (b) is a side elevation view of the test strip 4.

FIG. 5(a) shows the test tube 1 whose bottom section 1a has an inclined plane. FIG. 5(b) shows the test tube 1 whose bottom section 1a is flat.

FIG. 6(a) shows an example of a test strip 4. FIG. 6(b) shows an example of a test strip 4. FIG. 6(c) shows an example of a test strip 4.

FIG. 11 (b) is a side elevation view of the test strip 4 shown in FIG. 10.

DESCRIPTION OF THE PREFERRED EMBODIMENTS

Figure 1:
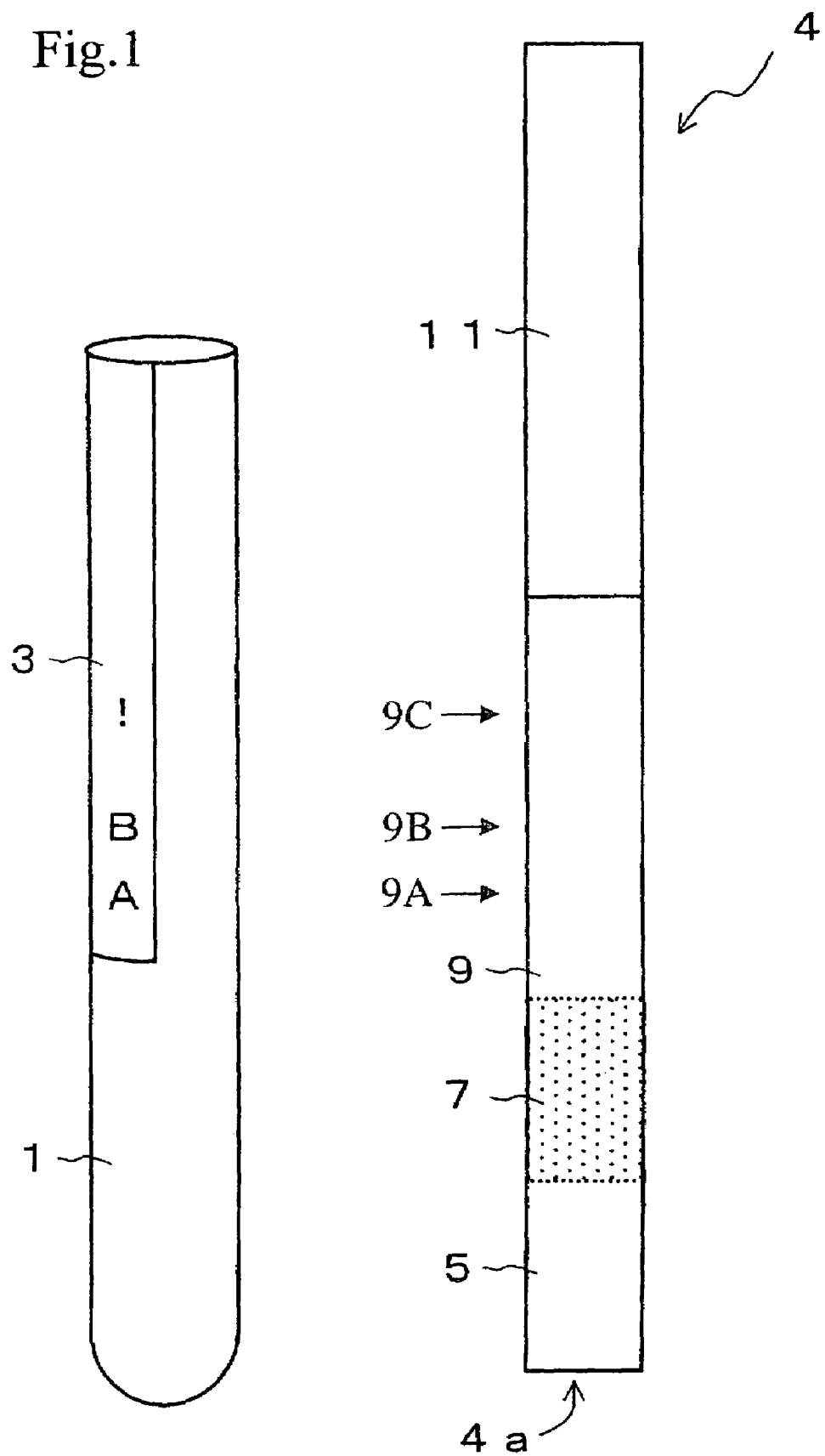
FIG. 1 shows a test kit for immunochromatography of the first embodiment of the present invention.

A test kit for immunochromatography of the present embodiment is equipped with a test strip for immunochromatography and a test tube in which a sample can be accommodated. This test strip is used by inserting into the test tube from one end side. The test strip has a first detection zone for detecting a first analyte in a sample. The test tube has an indicator. This indicator shows the classification of the analyte which is detected in the first detection zone. This indicator is located at the position corresponding to the first detection zone of the test strip.

Therefore, according to the present embodiment, a test kit for immunochromatography is provided. This test kit can be easily prepared at a low cost and perform the precise determination is provided.

Hereinafter, the present embodiment will be explained with reference to drawings. The drawings are used for the convenience of explanation, and the scope of the present invention is not limited to embodiments shown in the drawings.

1. First Embodiment

Figure 2:
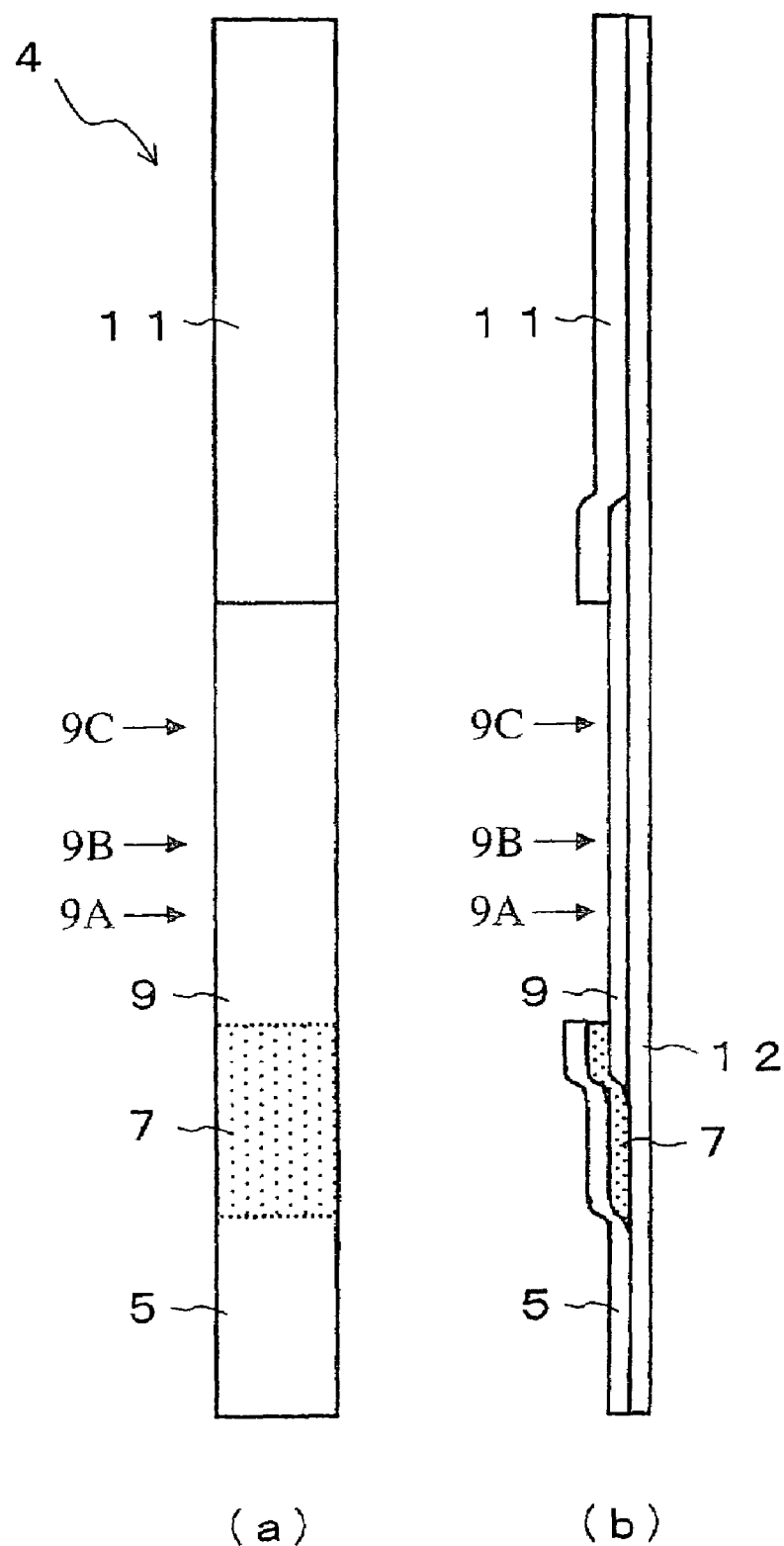
FIG. 2 (a) is a plan view of the test strip 4.

FIG. 1 shows a test kit for immunochromatography of the first embodiment of the present invention. This test kit is equipped with a test tube 1 for containing a sample and a test strip 4. The test strip 4 is used by inserting it into the test tube 1 from the one end side 4a. FIG. 2 (a) is a plan view of the test strip 4. FIG. 2 (b) is a side elevation view of the test strip 4.

As shown in FIG. 2 (b), the test strip 4 is equipped with a sample receiving member 5, a label holding member 7, a chromatography membrane 9 and an absorbance member 11 on a substrate 12. The substrate 12 has an adhesive layer on its surface.

The substrate 12 is composed of a plastic plate.

The sample receiving member 5 is composed of nonwoven fabric made of rayon.

The label holding member 7 is composed of an nonwoven fabric made of glass fiber.

The chromatography membrane 9 is composed of a porous body of nitrocellulose.

The absorbance member 11 is composed of an nonwoven fabric made of cellulose.

The label holding member 7 is disposed in contact with the sample receiving member 5. The label holding member 7 holds a labeling substance which generates an antigen-antibody reaction with the analyte in a sample.

The chromatography membrane 9 is disposed in contact with the label holding member 7. The chromatography membrane 9 has two detection zones (a first detection zone and a second detection zone) and a control zone.

The absorbance member 11 is disposed so that it is in contact with the chromatography membrane 9.

In the chromatography membrane 9, a first detection zone 9A, a second detection zone 9B and a control zone 9C are formed from the upstream side of the sample development direction. They are in a linear shape.

The label holding member 7 holds a first labeling substance, a second labeling substance and a labeling substance for control.

In the first detection zone 9A, an anti-influenza A virus antibody (hereinafter, referred to as anti-Flu A antibody) is fixed. In the second detection zone 9B, anti-influenza B virus antibody (hereinafter, referred to as anti-Flu B antibody) has been fixed. In the control zone 9C, biotin is fixed.

The first labeling substance is an anti-Flu A antibody which has been labeled by a blue colored latex particle.

The second labeling substance is an anti-Flu B antibody which has been labeled by a blue colored latex particle.

The labeling substance for control is avidin which has been labeled by a red colored latex particle.

The anti-Flu A antibody is specifically bound to influenza A virus (hereinafter, referred to as Flu A virus) which is the first analyte.

The anti-Flu B antibody is specifically bound to influenza B virus (hereinafter, referred to as Flu B virus) which is the second analyte.

For example, when a sample containing Flu A virus is added to the sample receiving member 5, the sample moves within the sample receiving member 5 by capillary phenomenon and reaches to the label holding member 7. The anti-Flu A antibody which has been labeled in the label holding member 7 specifically recognizes Flu A virus, and binds to the virus by an antigen-antibody reaction. The complex of antibody and virus is formed. This complex moves to the chromatography membrane 9, and reaches to the first detection zone 9A. The anti-Flu A antibody which has been fixed in the first detection zone 9A specifically recognizes Flu A virus, and traps the complex. When the complex is trapped, in the first detection zone 9A, a blue colored line emerges and Flu A virus is detected by visual observation.

Labeling avidin held in the label holding member 7 is not trapped by anti-Flu A antibody and anti-Flu B antibody fixed in the chromatography membrane 9. However, it is trapped by biotin which has been fixed in the control zone 9C. When avidin is trapped, in the control zone 9C, a red colored line emerges, and it is visually observed that avidin has reached to the control zone 9C. The control zone 9C is provided at the downstream side of the first detection zone 9A and the second detection zone 9B. Therefore, by recognizing the red colored line, it is recognized that the sample has passed through the first detection zone 9A and the second detection zone 9B.

The test tube 1 is composed of glass.

In the test tube 1, a label sheet 3 is pasted. The label sheet 3 has the indicator "A", the indicator "B" and the indicator "!".

The indicator "A" is disposed at the position corresponding to the first detection zone 9A of the test strip 4, and indicates the classification of the analyte detected in the first detection zone 9A. The indicator "A" indicates the emerging position of the detection line in the first detection zone 9A.

The indicator "B" is disposed at the position corresponding to the second detection zone 9B of the test strip 4, and indicates the classification of the analyte detected in the second detection zone 9B. The indicator "B" indicates the emerging position of the detection line in the second detection zone 9B.

The indicator "!" is disposed at the position corresponding to the control zone 9C of the test strip 4, and indicates the emerging position of the detection line of the control zone 9C.

The label sheet 3 is a sheet on which "A", "B" and "!" have been printed at the predetermined position of a transparent base member.

The label sheet 3 performs the alignment in the vertical direction between the label sheet 3 and the test tube 1 by corresponding the upper end to the inlet of the test tube 1.

A method for utilizing a test kit of the present embodiment will be explained below with reference to FIG. 3.

First, the specimen such as nasal cavity aspirate of the patient or the like is diluted in a development solvent, and the predetermined amount of a prepared sample 13 is injected within the test tube 1.

Next, the test strip 4 is inserted into the test tube 1 from the one end 4a, and the one end 4a is made in contact with the bottom section 1a of the test tube 1 (It should be noted that herein termed "bottom section" means a portion having rounded corner of the test tube 1).

In this state, it is left as it is for about 10 to 20 minutes, the sample 13 moves sequentially to the sample receiving member 5, the label holding member 7, the chromatography membrane 9 and the absorbance member 11 in this order by capillarity phenomenon.

At the time when the sample 13 passes through the label holding member 7, the labeling substances (the first labeling substance, the second labeling substance and the labeling substance for control) held by the label holding member 7 are eluted in the development solvent.

In the case where Flu A virus is contained in a sample, a blue colored line emerges in the first detection zone 9A.

In the case where Flu B virus is contained in a sample a blue colored line emerges in the first detection zone 9B.

Regardless of whether or not there is virus, the red colored line emerges in the control zone 9C.

Figure 4:
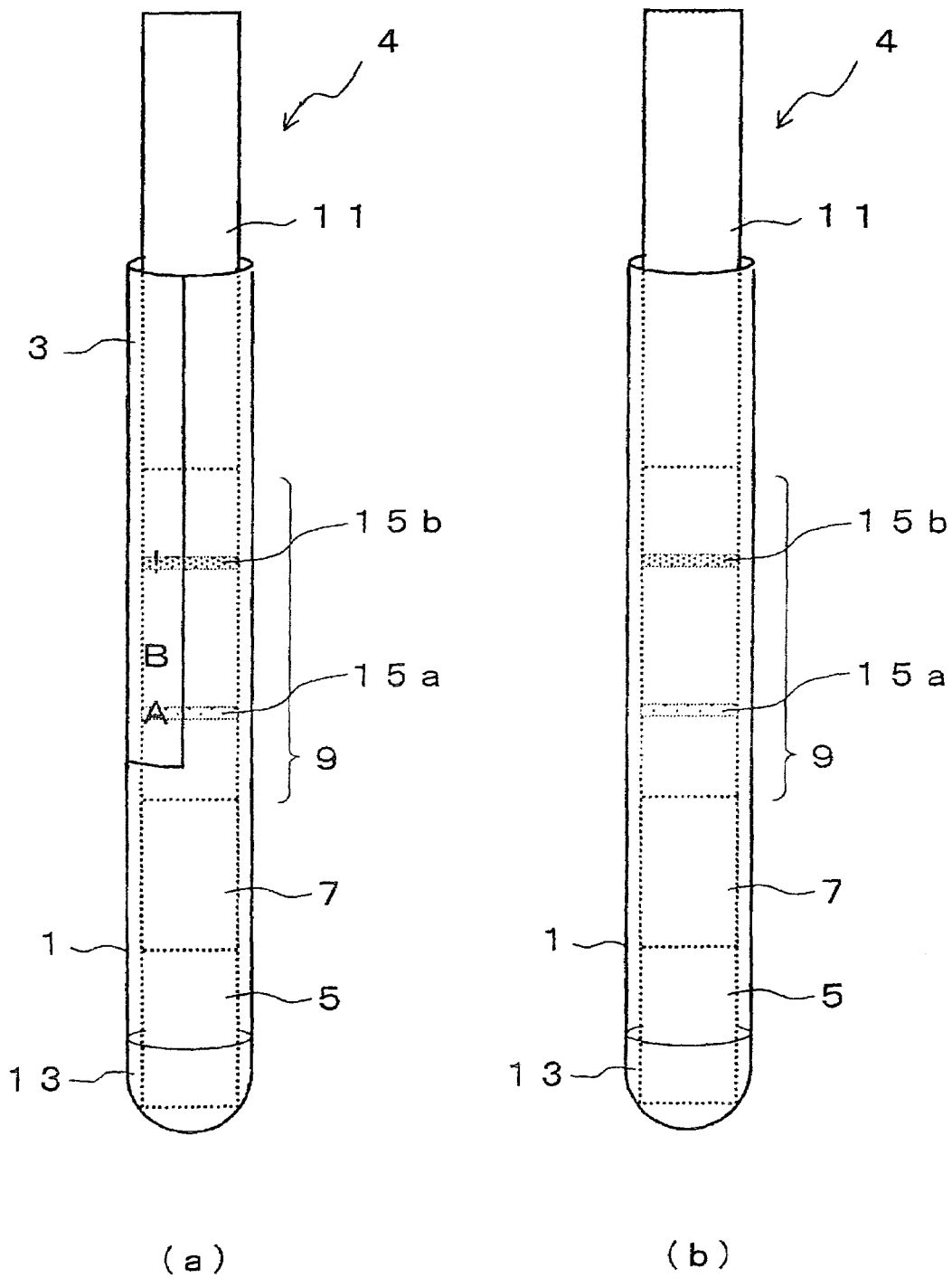
FIG. 4(a) shows the measurement results in the case where the label sheet 3 exists.
FIG. 4(b) shows the measurement results in the case where the label sheet 3 does not exist.

Here, with reference to FIG. 4, the measurement results in the case where the label sheet 3 exists (FIG. 4(a)) and in the case where the label sheet 3 does not exist (FIG. 4 (b)) are compared. FIG. 4 (a) corresponds to a test kit of the present invention. Either of FIGS. 4 (a) and (b) indicates the results in the case where only Flu A virus is contained in a sample.

First, with reference to FIG. 4 (b), it is understood that a blue colored line 15a and a red colored line 15b emerge in the test strip 4. It is understood that the red colored line 15b has emerged in the control zone 9C from the color. But it is difficult to determine which of the first detection zone 9A or the second detection zone 9B the blue colored line 15a has emerged in.

Next, with reference to FIG. 4 (a), it is understood that the letter "A" within the label sheet 3 pasted on the test tube is positioned at the position corresponding to the blue colored line 15a. It can be easily determined that the blue colored line 15a emerges in the first detection zone 9A in a test kit of the present invention by this letter "A" existing there, and it is understood that only Flu A virus has been contained in the sample.

In this way, according to the present embodiment, the classification of the emerged line can be precisely identified.

Up to this point, the specified embodiment has been exemplified and explained. However, the present invention is not limited to this embodiment, and a variety of modifications can be carried out.

The analyte is not particularly limited if it is a substance for generating an antigen-antibody reaction with an antibody.

Cell (such as bacterium, protist, mycosis and the like), virus, protein, polysaccharides and the like are listed as an analyte. For example, in addition to the above-mentioned influenza viruses, parainfluenza virus, RS virus, mycoplasma pneumoniae, rotavirus, Calici virus, corona virus, adenovirus, enterovirus, herpes virus, human immunodeficiency virus, hepatitis virus, pathogenic virus of severe acute respiratory syndrome (SARS), *E. coli, Staphylococcus aureus, Streptococcus pneumoniae, Streptococcus pyogenes*, Plasmodium, and the others such as digestive system diseases, central nervous system diseases, pathogens of a variety of diseases such as hemorrhagic fever and the like, metabolites thereof, carcinoembryonic antigen, tumor markers such as CYFRA and the like, hormones and the like are exemplified.

For the base member 12, a variety of materials such as paper, glass or the like can be used.

The sample receiving member 5 can be formed by a variety of materials such as glass fiber, cellulose fiber or the like.

The label holding member 7 can be formed by a variety of materials such as cellulose fiber or the like.

The chromatography membrane 9 can be formed by a variety of materials such as nylon (for example, modified nylon to which amino group that may have carboxyl group or alkyl group as a substituent has been introduced), poly(vinylidene difluoride) (PVDF), cellulose acetate or the like.

The absorbance member 11 can be formed by a variety of materials such as glass fiber or the like.

For the sample receiving member 5, the label holding member 7, the chromatography membrane 9 and the absorbance member 11, a material having a variety of structure which is capable of developing the sample by capillary phenomenon can be used except for nonwoven fabric or porous body.

The chromatography membrane 9 may be equipped with only one of the detection zone, or may be equipped with two or more.

The chromatography membrane 9 may not be equipped with the control zone.

The detection zone/control zone may not be in a linear shape; for example, it may be formed in a circular shape or in a square shape.

The label holding member 7 may hold only one types of labeling substance, or may hold two types or more.

The label holding member 7 may not hold a labeling substance for control.

The labeling substance may be labeled by a latex particle colored by colors except for blue or red, metal colloid particle such as gold and the like, pigment molecule and the like.

In the case where there exist two types or more of the labeling substances, the respective labeling substances may be labeled by colors different from each other, or may be labeled by the same color.

The labeling substance and labeling substance for control may be labeled by colors different from each other, or may be labeled by the same color.

According to the present embodiment, even in the case where the respective labeling substances have been labeled by the same color, the classification of the emerged lines can be precisely carried out.

For a substance for fixing in the detection zone, a variety of antibodies or antigens can be used. In the case where the analyte is an antigen, an antibody which can be bound to this antigen is used for a substance for fixing. In the case where the analyte is an antibody, for a substance for fixing, an antigen or antibody which can be bound to this antibody is used.

The labeling substance can have an antibody or antigen. In the case where the analyte is an antigen, the labeling substance is equipped with an antibody which can be bound to this antigen by an antigen-antibody reaction. In the case where the analyte is an antibody, the labeling substance is equipped with an antigen or antibody which generates an antigen-antibody reaction with this antibody.

Avidin may be fixed in the control zone, and the labeling substance for control may be equipped with biotin.

Furthermore, a control substance for fixing and a labeling substance for control in the control zone may be a certain combination except for the combination of biotin and avidin. For example, it may be a combination binding by an antigen-antibody reaction. Concretely, the labeling substance for control may be equipped with an antigen, and an antibody which generates an antigen-antibody reaction with this antigen may be fixed on the control zone. It may be contrary to this. As a combination of this antigen and antibody, the combination of hapten and anti-hapten antibody and the like are exemplified.

As for a labeling substance for control, it is preferable that it is equipped with a substance which is not bound to the analyte and a substance for fixing of the detection zone.

The test tube 1 may be formed by plastic, polystyrene and the like.

Figure 5:
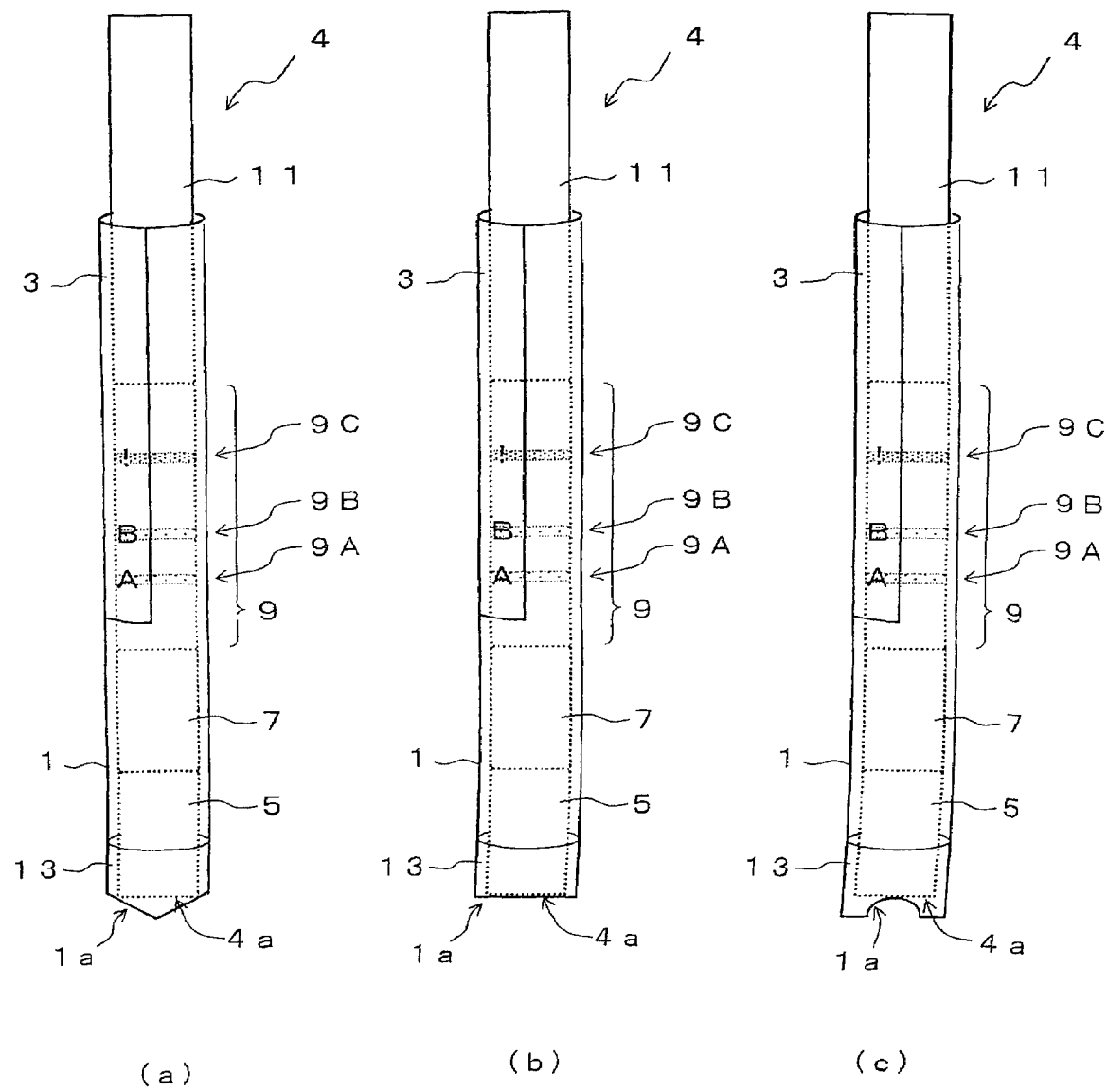
FIG. 5 (c) shows the test tube 1 whose bottom section 1a is projected into the inside of the test tube.

The bottom section 1a of the test tube 1 may have an inclined plane as shown in FIG. 5 (*a*), it may be flat as shown in FIG. 5 (*b*), or it may be projected into the inside of the test tube as shown in FIG. 5 (*c*). In any one of these cases, the test strip 4 and the test tube 1 is aligned in the vertical direction.

The label sheet 3 of the test tube 1 may be aligned in the vertical direction so that the lower end of the label sheet 3 is aligned to the lowest section of the test tube 1. The label sheet 3 may be an opaque. Instead of pasting on the test tube 1 the label sheet 3 onto which the indicator of the classification has been printed, this indicator may be directly printed on the test tube. The indicator may be sculptured on the test tube. The indicator may be the name of the analyte or the like except for an alphabet or a symbol. The dot, line or the like may be attached at the position corresponding to the detection zone/control zone. For example, if the dots have been pointed, respectively at the position corresponding to the first detection zone 9A, the second detection zone 9B and the control zone 9C, it is understood that these 3 points indicate the first detection zone 9A, the second detection zone 9B and the control zone 9C from the lower position sequentially in this order. Such a dot, line or the like are also included in "indicator".

For example, in the case where only the labeling substance for control is labeled by a different color as the above-described embodiment, the indicator for indicating the control zone may not be attached. This is because it is understood that the line has emerged in the control zone from the color emerging, even if there is no indicator for the control zone.

As the test strip 4, except for the test strip shown in FIG. 2, a test strip shown in FIGS. 6 (*a*)-(*c*) and the like may be available.

In the test strip shown in FIG. 6 (*a*), the sample receiving member 5 is disposed so that the sample receiving member 5 covers the label holding member 7, and further is in contact with the chromatography membrane 9.

In the test strip shown in FIG. 6 (*b*), the label holding member 7 is disposed via an interval with the chromatography membrane 9, and the sample receiving member 5 is disposed so that the sample receiving member 5 covers the label holding member 7 and is in contact with the chromatography membrane 9.

In the test strip shown in FIG. 6 (*c*), the label holding member 7 is disposed via an interval with the chromatography membrane 9, and the development member 17 is disposed so that the development member 17 is contact with the label holding member 7 and the chromatography membrane 9.

The development member 17 can be constituted by a variety of unwoven materials such as rayon, glass fiber, cellulose fiber or the like similar to the sample receiving member 5.

In the constitution shown in FIG. 6 (b), (c), since the member in which the development speed of a sample is high is sandwiched between the label holding member 7 and the chromatography membrane 9, the elution of the labeling substance within the label holding member 7 is speeded up, and the swift measurement can be carried out.

Figure 3:
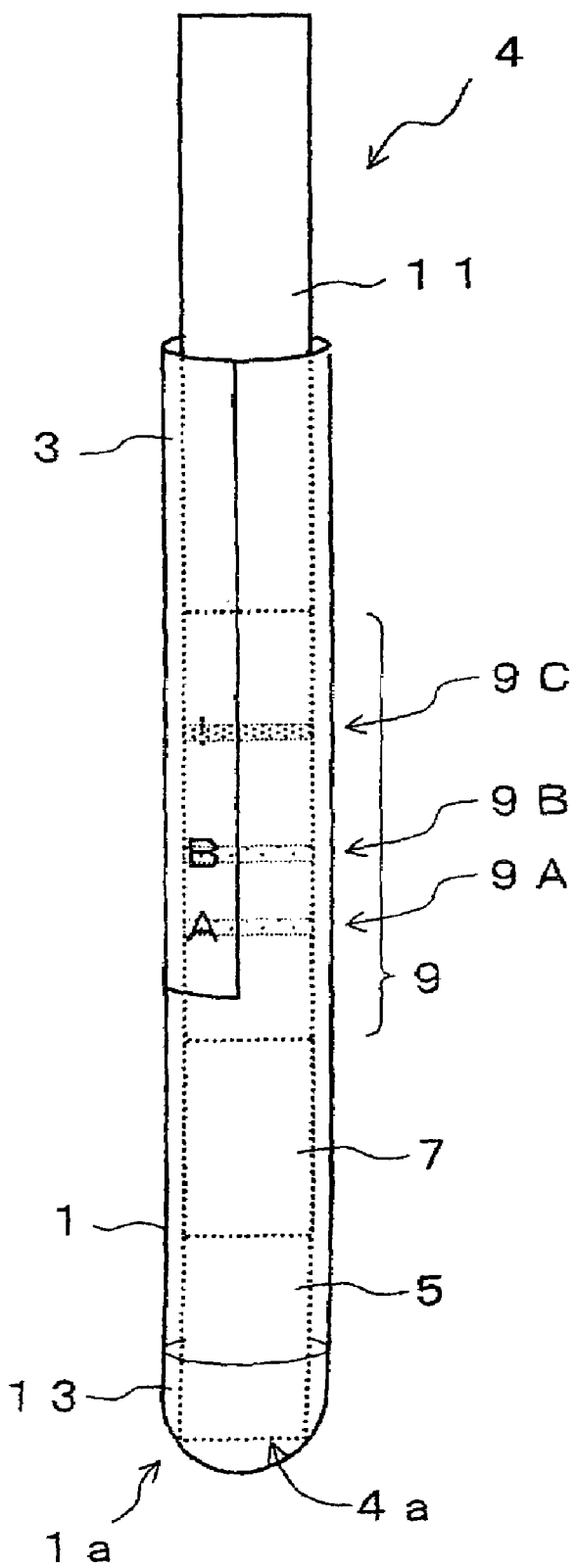
FIG. 3 shows a method for utilizing a test kit of FIG. 1.
Figure 7:
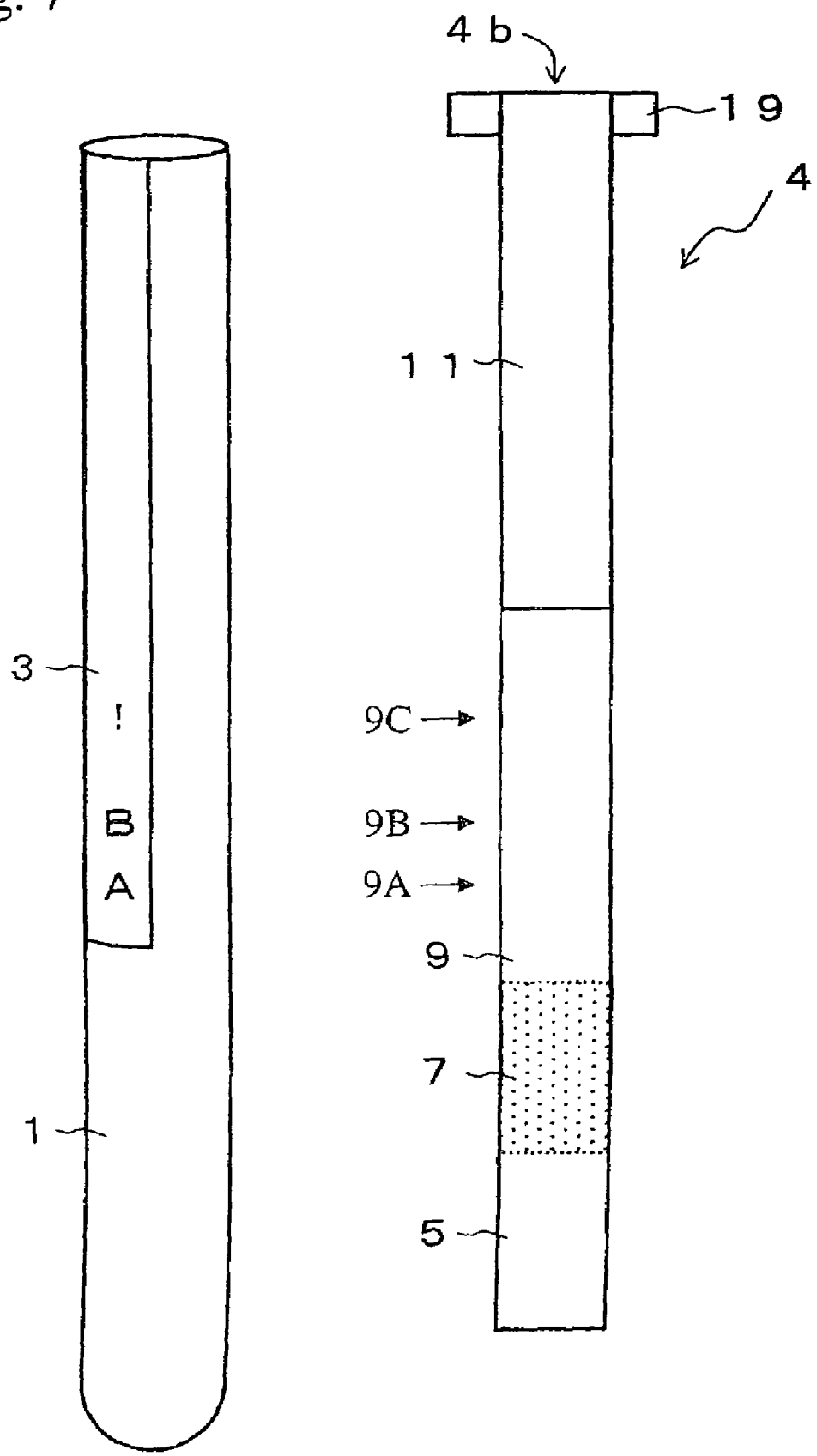
FIG. 7 shows the test strip whose length is longer than the length of the test strip 4 by providing a convex section 19.
Figure 8:
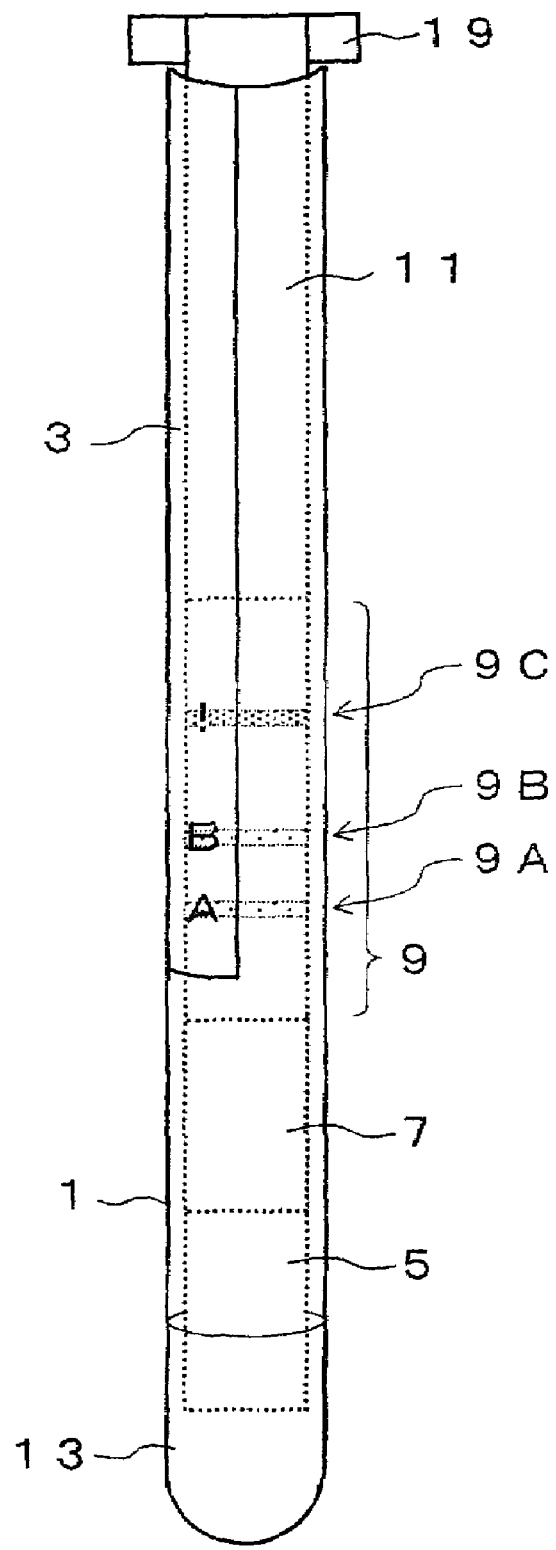
FIG. 8 shows a method for utilizing the test strip of FIG. 7.

In the above-described embodiment, as shown in FIG. 3, both of the test strip 4 and the test tube 1 were aligned in the vertical direction by making the one end 4a of the test strip 4 in contact with the bottom section 1a of the test tube 1. However, as shown in FIG. 7, the length of the test tube 1 may be made longer than the length of the test strip 4 by providing a convex section 19 at another end (other end) 4b of the test strip 4. Owing to this, as shown in FIG. 8, the convex section 19 of the test strip 4 is caught on the inlet of the test tube 1, and the alignment of both in the vertical direction can be carried out. The convex section 19 may be formed on the base member 12 itself, or may be formed by pasting another member (plastic plate or the like) on the rear surface of the base member 12.

The convex section 19 may be formed in a shape spanning over the inlet of the test tube 1 as shown in FIG. 8.

Figure 9:
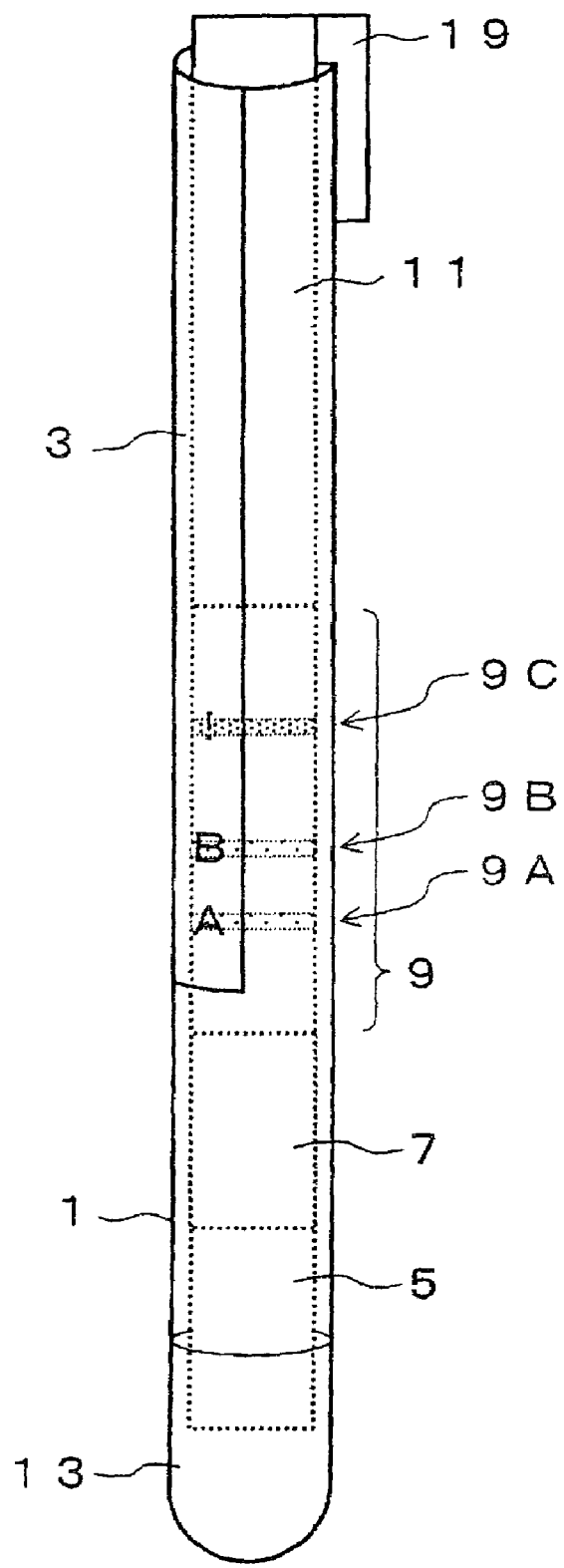
FIG. 9 shows the test strip which has a hooked shaped convex section 19.

The convex section 19 may be formed in a hooked shape so that it is hanged up on the side wail of the test tube 1 as shown in FIG. 9.

The sample may be added to the sample receiving member 5 of the test strip 4 before the test strip 4 is contained in the test tube 1. In this case, the test strip 4 is inserted into the test tube 1 after the sample has been added, and the classification of the line of the detection zone can be confirmed.

2. Second Embodiment

Figure 10:
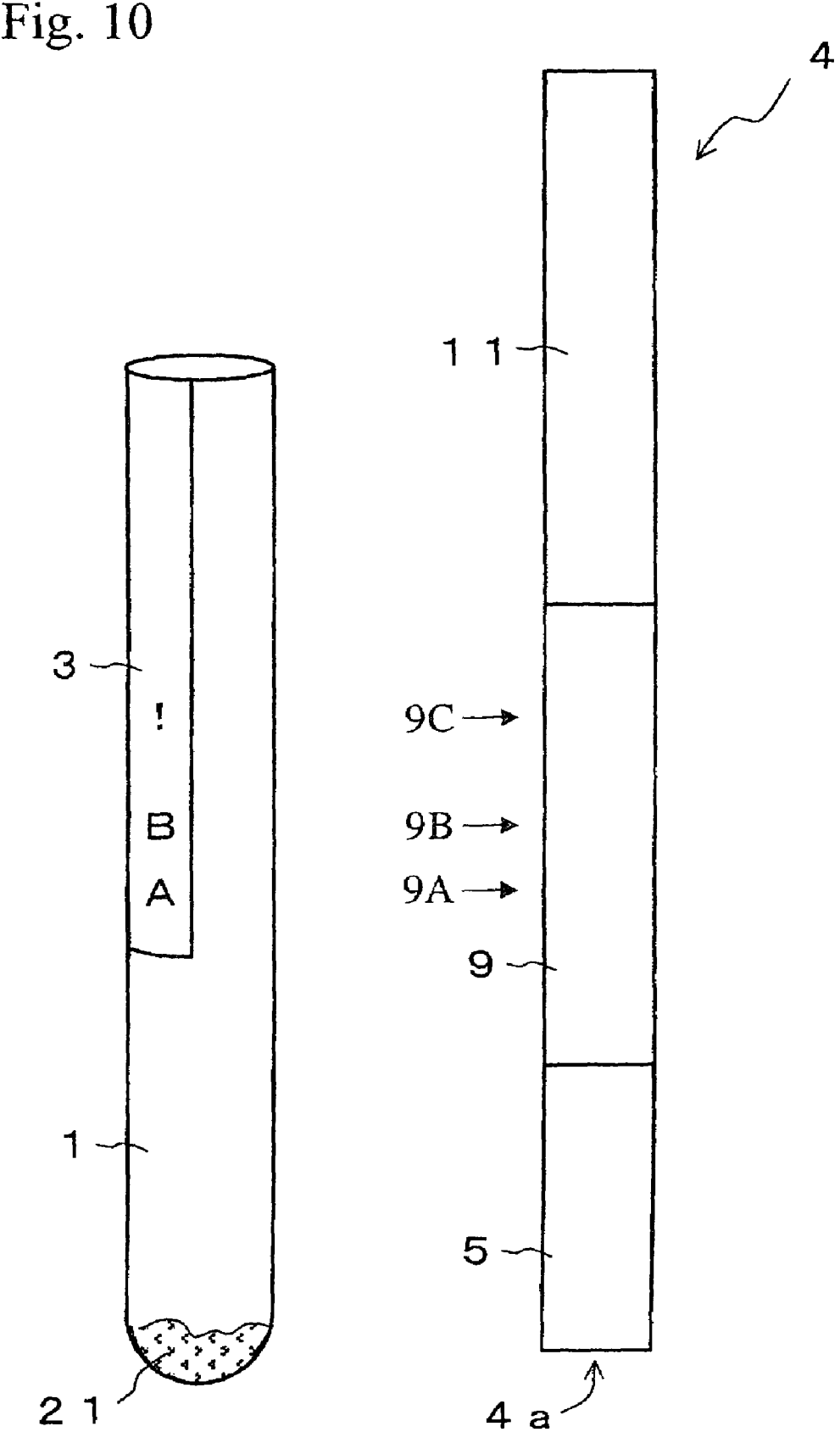
FIG. 10 shows a test kit for immunochromatography of the second embodiment of the present invention.
Figure 11:
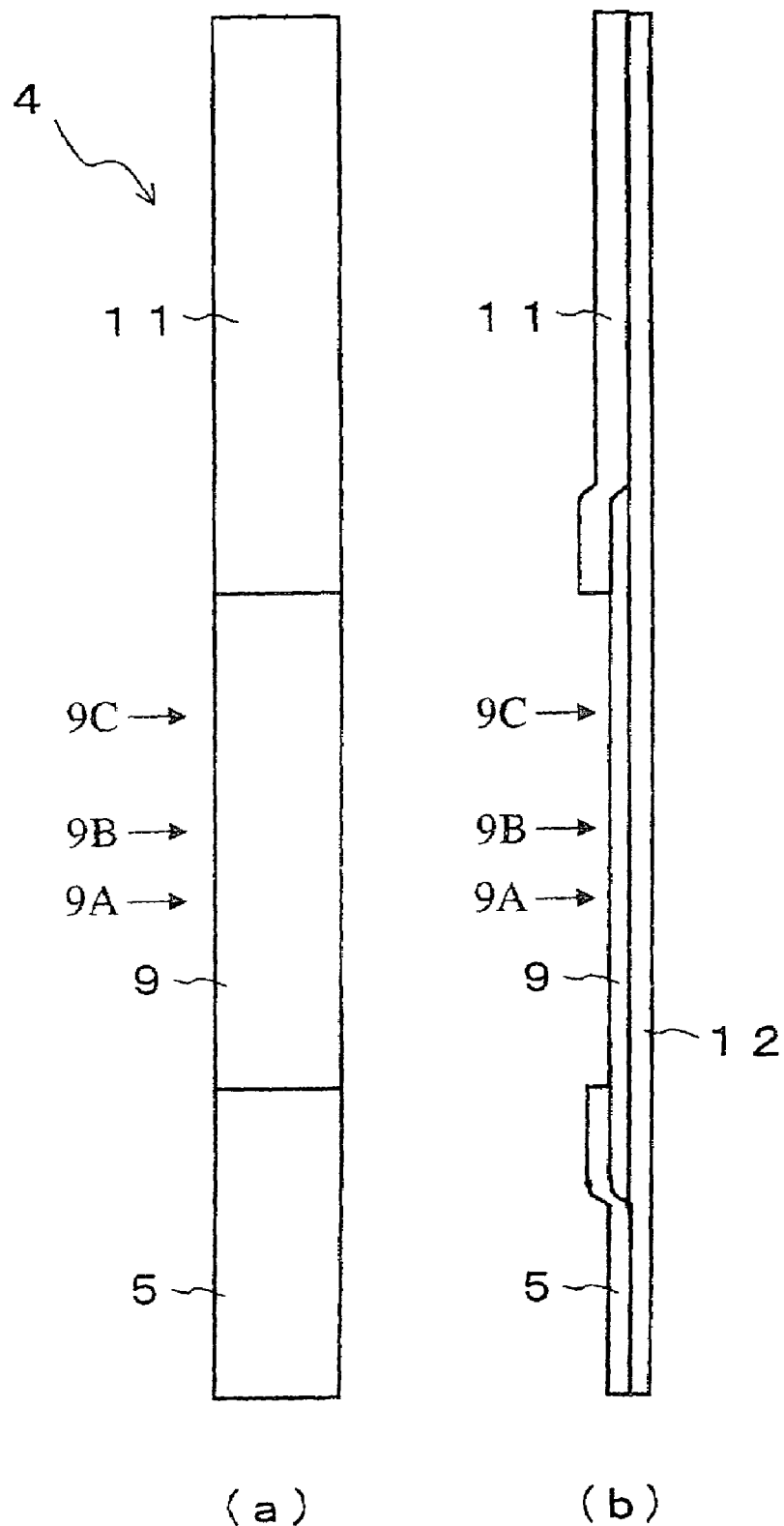
FIG. 11 (a) is a plan view of the test strip 4 shown in FIG. 10.

FIG. 10 shows a test kit for immunochromatography of the second embodiment of the present invention. FIG. 11 (a) is a plan view of the test strip 4 shown in FIG. 10. FIG. 11 (b) is a side elevation view of the test strip 4 shown in FIG. 10.

This test kit is different when compared to the first embodiment in that the test strip 4 does not have the label holding member 7, and that the test tube 1 contains the labeling substance 21. In the test strip 4, as shown in FIG. 11 (b), the sample receiving member 5 and the chromatography membrane 9 are in contact with each other. In the labeling substance 21, the first labeling substance, the second labeling substance and the labeling substance for control are contained.

Figure 12:
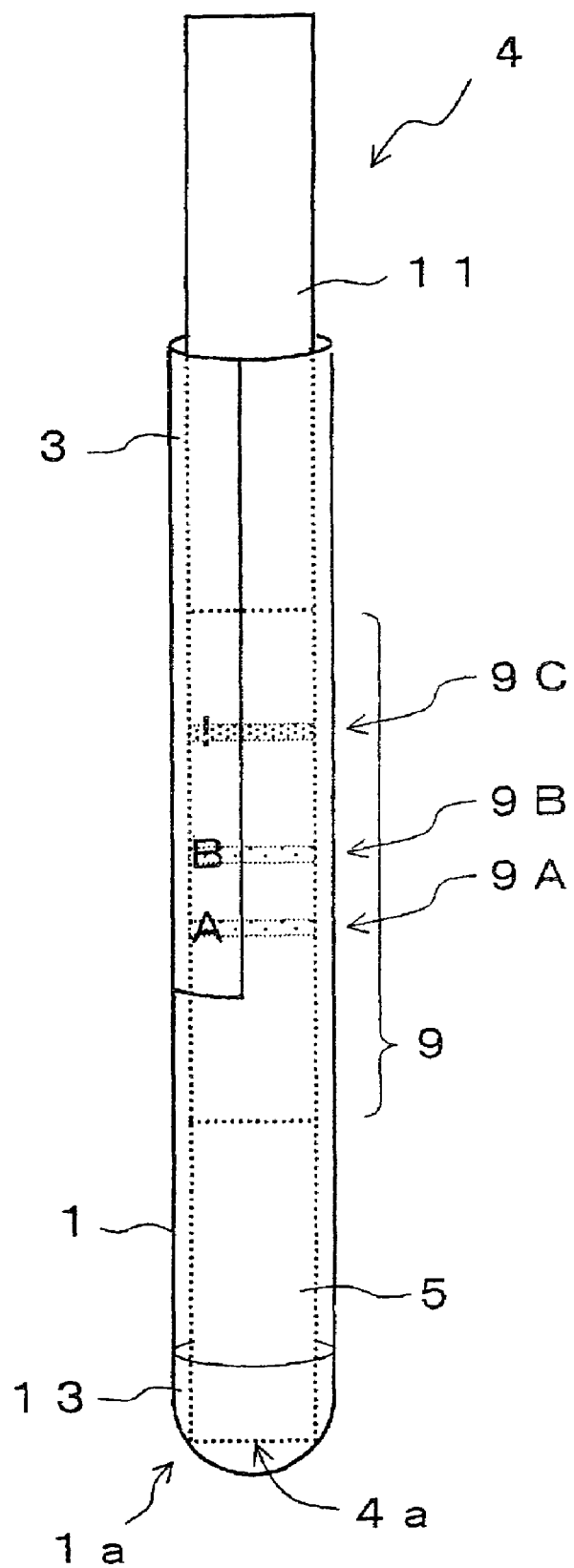
FIG. 12 shows a method for utilizing a test kit of FIG. 10.

Next, a method for utilizing a test kit of the present embodiment will be explained below with reference to FIG. 12.

First, the specimen such as nasal cavity aspirate of the patient or the like is diluted in a development solvent, and the predetermined amount of the prepared sample 13 is injected within the test tube 1. Next, the sample 13 and the labeling substance 21 which is contained in the test tube 1 are sufficiently agitated. Next, the test strip 4 is inserted into the test tube 1 from the one end 4a, and the one end 4a is made in contact with the bottom section 1a of the test tube 1. Owing to this, the test strip 4 and the test tube 1 are aligned in the vertical direction. In this state, it is left as it is for about 10 to about 20 minutes, the sample 13 moves sequentially to the sample receiving member 5, the chromatography membrane 9 and the absorbance member 11 in this order by capillarity phenomenon. In the case where Flu A virus or Flu B virus is contained in a sample, a blue colored line emerges in the first detection zone 9A or the second detection zone 9B by the action described with respect to the first embodiment. Regardless of whether or not there is virus, the red colored line emerges in the control zone 9C.

Since the test tube has an indicator that indicates the detection zone in a test kit of the present embodiment, the classification of the emerged line can be precisely carried out. A test kit of the present embodiment can be also modified in a variety of ways explained in the first embodiment.

What is claimed is:

1. A test kit for immunochromatography comprising:
   a test strip comprising a detection zone for detecting an analyte in a sample; and
   a test tube for accommodating the test strip,
   wherein the test tube comprises:
   an elongated and bottomed tube body with an opening at one end; and
   an indicator arranged on the test tube body at a position corresponding to the detection zone of the test strip when the test strip is accommodated in the test tube body, and
   wherein the test tube body is shorter than the test strip such that a part of the test strip projects upward from the opening when the test strip is accommodated in the test tube body.

2. The test kit according to claim 1, wherein the sample is accommodated in the test tube.

3. The test kit according to claim 1, wherein the indicator indicates a type of the analyte detected by the detection zone.

4. The test kit according to claim 1, wherein the test strip comprises a second detection zone for detecting a second analyte in the sample, and the test tube comprises a second indicator at a position corresponding to the second detection zone.

5. The test kit according to claim 4, wherein the second indicator indicates a type of the second analyte detected by the second detection zone.

6. The test kit according to claim 1, wherein the test strip comprises a control zone for checking whether or not the sample passes through the detection zone, and the control zone is located at a downstream side of the detection zone in a sample development direction.

7. The test kit according to claim 6, wherein the test tube comprises a second indicator at a position corresponding to a position of the control zone.

8. The test kit according to claim 7, wherein the second indicator indicates the control zone.

9. The test kit according to claim 4, wherein the test strip comprises a control zone for checking whether or not the sample passes through both the detection zone and the second detection zone, and the control zone is located at a downstream side of a sample development direction in comparison with the detection zone and the second detection zone.

10. The test kit according to claim 9, wherein the test tube comprises a third indicator at a position corresponding to a position of the control zone.

11. The test kit according to claim 10, wherein the indicator indicates a type of the analyte detected by the detection zone, the second indicator indicates a type of the second analyte detected by the second detection zone, and the third indicator indicates the control zone.

12. The test kit according to claim 6, wherein the test strip comprises a sample receiving member, a label holding member comprising a first labeling substance which can specifically bind to the analyte, and a control labeling substance, and a chromatography membrane comprising the detection zone and the control zone, wherein a first substance which can specifically bind to the analyte is fixed in the detection zone, the control zone can capture the control labeling substance, and the sample receiving member, the label holding member and the chromatography membrane are set on a substrate.

13. The test kit according to claim 9, wherein the test strip comprises a sample receiving member, a label holding member comprising a first labeling substance which can specifically bind to the analyte, a second labeling substance which can specifically bind to the second analyte, and a control labeling substance, and a chromatography membrane comprising the first detection zone, the second detection zone and the control zone, wherein a first substance which can specifically bind to the first analyte is fixed in the first detection zone, a second substance which can specifically bind to the first analyte by antigen-antibody reaction is fixed in the second detection zone, the control zone can capture the control labeling substance, and the sample receiving member, the label holding member and the chromatography membrane are set on a substrate.

14. The test kit according to claim 6, wherein the test tube accommodate a labeling substance which can specifically bind to the analyte and a control labeling substance, the test strip comprises the sample receiving member and the chromatography membrane comprising the detection zone where a first substance is fixed and the control zone which can capture the control labeling substance, and the sample receiving member and the chromatography membrane are set on a substrate.

15. The test kit according to claim 9, wherein the test tube accommodate a first labeling substance which can specifically bind to the analyte, a second labeling substance which can specifically bind to the second analyte and a control labeling substance, the test strip comprises the sample receiving member and the chromatography membrane comprising the first detection zone where a first substance is fixed, the second detection zone where a second substance is fixed, and the control zone which can capture the control labeling substance, and the sample receiving member, the label holding member and the chromatography membrane are set on a substrate.

16. The test kit according to claim 1, wherein a label sheet comprising the indicator is attached to the test tube.

17. The test kit according to claim 1, wherein the indicator is printed on the test tube.

18. A test tube which can accommodate a test strip for immunochromatography, comprising
    an elongated bottomed tube body with an opening at one end;
    an indicator that indicates a type of an analyte detected by a detection zone of the test strip and is arranged on the test tube body at a position corresponding to the detection zone of the test strip when the test strip is accommodated in the test tube body; and
    wherein the test tube body is shorter than the test strip such that a part of the test strip projects upward from the opening when the test strip is accommodated in the test tube body.

19. The test tube according to claim 18, further comprising a label sheet which comprises the indicator, wherein the label sheet is attached to the test tube body.

* * * * *